United States Patent
Qin et al.

(10) Patent No.: US 11,179,349 B2
(45) Date of Patent: Nov. 23, 2021

(54) USE OF TUMOR GENE METHYLATION REGULATOR AND ANTI-TUMOR DRUGS

(71) Applicants: Yang Qin, Sichuan (CN); Qing Dong, Sichuan (CN)

(72) Inventors: Yang Qin, Sichuan (CN); Qing Dong, Sichuan (CN)

( * ) Notice: Subject to any disclaimer, the term of this patent is extended or adjusted under 35 U.S.C. 154(b) by 0 days.

(21) Appl. No.: 16/075,248

(22) PCT Filed: Jan. 24, 2017

(86) PCT No.: PCT/CN2017/072505
§ 371 (c)(1),
(2) Date: Aug. 3, 2018

(87) PCT Pub. No.: WO2017/133599
PCT Pub. Date: Aug. 10, 2017

(65) Prior Publication Data
US 2019/0046470 A1    Feb. 14, 2019

(30) Foreign Application Priority Data

Feb. 4, 2016  (CN) .......................... 201610078152.2

(51) Int. Cl.
| | |
|---|---|
| *A61P 35/00* | (2006.01) |
| *A61K 31/517* | (2006.01) |
| *A61K 31/122* | (2006.01) |
| *C07K 14/47* | (2006.01) |
| *A61K 31/337* | (2006.01) |
| *A61K 45/06* | (2006.01) |
| *A61K 31/513* | (2006.01) |
| *A61K 31/7068* | (2006.01) |
| *A61K 31/555* | (2006.01) |
| *A61K 31/704* | (2006.01) |

(52) U.S. Cl.
CPC .......... *A61K 31/122* (2013.01); *A61K 31/337* (2013.01); *A61K 31/513* (2013.01); *A61K 31/517* (2013.01); *A61K 31/555* (2013.01); *A61K 31/704* (2013.01); *A61K 31/7068* (2013.01); *A61K 45/06* (2013.01); *A61P 35/00* (2018.01); *C07K 14/4702* (2013.01)

(58) Field of Classification Search
CPC .. A61K 31/122; A61K 31/337; A61K 31/517; A61K 45/06; A61K 31/513; A61K 31/7068; A61K 31/704; A61K 31/555; A61P 35/00; C07K 14/4702
See application file for complete search history.

(56) References Cited

FOREIGN PATENT DOCUMENTS

| | | |
|---|---|---|
| CN | 102936271 A | 2/2013 |
| CN | 103301090 A | 9/2013 |

OTHER PUBLICATIONS

Karen Gelmon, Arlene Chan, Nadia Harbeck, The Role of Capecitabine in First-Line Treatment for Patients with Metastatic Breast Cancer, The Oncologist 2006;11 (suppl 1):42-51 (Year: 2006).*
Fu-Chi Kang, Pei-Jung Chen, Bo-Syong Pan, Meng-Shao Lai, Yung-Chia Chen, Bu-Miin Huang, Apoptotic effect of cordycepin combined with cisplatin and/or paclitaxel on MA-10 mouse Leydig tumor cells, OncoTargets and Therapy 2015:8 2345-2360 (Year: 2015).*
International Search Report of the International Searching Authority from corresponding Patent Cooperation Treaty (PCT) Application No. PCT/CN2017/072505, indicated completed on Apr. 28, 2017.
Written Opinion of the International Searching Authority from corresponding Patent Cooperation Treaty (PCT) Application No. PCT/CN2017/072505, indicated completed on Apr. 28, 2017.
Article entitled, "Dexamethasone inhibits paclitaxel-induced cytotoxic activity through retinoblastoma protein dephosphorylation in non-small cell lung cancer cells", written by Masato Morita, et al., accepted Sep. 18, 2006, published in the International Journal of Oncology in 2007.
Chinese article entitled, "Synthesis and anti-tum or actirities of dexamethasone derivative", written by Liu Chang, et al., from the Institute of Medicine in Chongqing Medical University, Mar. 2008.
Article entitled, "Vascular Endothelial Growth Factor Plus Epidermal Growth Factor Receptor Dual Targeted Therapy in Metastatic Colorectal Cancer: Synergy or Antagonism?", written by John L. Marshall, published by Hindawi Publishing Corporation Journal of Oncology, 2009.
Article entitled, "A Randomized Phase IIIB Trial of Chemotherapy, Bevacizumab, and Panitumumab Compared with Chemotherapy and Bevacizumab Alone for Metastatic Colorectal Cancer", written by J. Randolph Hecht, et al., published in Journal of Clinical Oncology, vol. 27, No. 5, Feb. 10, 2009.
Article entitled, "Chemotherapy, Bevacizumab, and Cetuximab in Metastatic Colorectal Cancer", written by Jolien Tol et al., published in New England Journal of Medicine, Mar. 2009.

* cited by examiner

*Primary Examiner* — Jason Deck
(74) *Attorney, Agent, or Firm* — Gardner, Linn, Burkhart & Ondersma LLP

(57) ABSTRACT

Disclosed is the use of a tumor gene methylation regulator in preparing anti-tumor drugs. Furthermore, the tumor gene methylation regulator can be used as a sensitizer to be combined with a tumor therapeutic drug for preparing anti-tumor drugs.

10 Claims, 5 Drawing Sheets

USE OF TUMOR GENE METHYLATION REGULATOR AND ANTI-TUMOR DRUGS

CROSS REFERENCE TO RELATED APPLICATIONS

The present application claims the priority benefits of International Patent Application No. PCT/CN2017/072505, filed Jan. 24, 2017, and claims benefit of Chinese patent application CN 201610078152.2, filed on Feb. 4, 2016.

BACKGROUND OF THE INVENTION

The present disclosure pertains to the field of tumor treatment, and specifically relates to new use of a tumor gene methylation regulator and anti-tumor drugs.

The process of tumorigenesis is complicated. The study of mechanism of tumorigenesis suggests that changes in human genetics, gene epigenetics or so forth may also be one of the causes of malignant tumors. Genetic changes such as gene mutations and deletions can lead to structural and functional disruption of the coding regions. The changes in gene epigenetics do not cause changes in DNA sequences, but result in changes in transcriptional level through the chemical modification of DNA itself, which may affect the expression of genes so as to control the DNA function. DNA methylation is one of the most common epigenetic modifications of DNAs of mammals, and it is also a hot topic of current interest in tumor biology. CpG islands in promoter regions of genes are generally unmethylated in normal states. When they are methylated, it often leads to silencing of gene transcription, causing loss of functions of important genes such as tumor suppressor genes, DNA repair genes and so on, thereby resulting in abnormal control of growth and differentiation of normal cells as well as DNA damages that cannot be repaired in time, which are related to the formation of a variety of tumors. DNA methylation is reversible. For example, DNA methylation regulators can be used to demethylate some important genes to restore their normal functions. Thus, inhibition of the activity of DNA methyltransferases has become a new research idea for the prevention and treatment of tumors.

A large number of literatures have reported that promoters of tumor suppressor genes involved in the inhibition of cell proliferation, repair of DNA damage and inhibition of tumor metastasis in human breast cancers, such as p16INK4A, p14ARF, p15, CCDN2, DAP, MGMT, hMLH1, GSTP1, RARβ₂, APC, ERβ, CDH1, and CDH13, are silenced by hypermethylation. An important mechanism leading to the methylation of tumor suppressor genes is the high expression of DNA methyltransferases in breast cancer cells.

Known DNA methyltransferase inhibitors include 5-azacytidine (azacitidine, 5-Aza-CR) and 5-aza-2-deoxycytidine (5-Aza-CdR). Their action mechanism is considered to inhibit DNA methylation both by replacing cytosine during DNA replication process and by inhibiting the activity of DNMT after forming a covalent bond with DNMT. They are widely used to study the biological process of DNA methylation and to treat acute myeloid leukemia and myelodysplastic syndrome (MDS). However, these two drugs are limited in clinical application due to their side effects such as mutagenesis, cytotoxicity, and myelosuppression.

In addition to DNA methyltransferases, an important coenzyme, i.e., S-adenosyl methionine (abbreviation: SAM), is required in the DNA methylation modification process to be involved in transmethylation reaction. It plays an important role in the transmethylation due to its "active methyl group". Currently, it has been known that SAM is involved in more than 40 in-vivo metabolic reactions, wherein the methyl group of S-adenosylmethionine is transferred to substrates such as nucleic acids, proteins and fatty acids. In the United States, a product has been sold as a nutritional supplement under the name of SAM, which has the effects of improving mood, maintaining liver and making joints comfortable.

Cordyceps is a special traditional Chinese medicine that is distributed in Tibet, Qinghai, Sichuan, Yunnan, and Gansu Provinces of China. The studies on cordyceps have been carried out for many years, and a great deal of results have been obtained, wherein the main ingredient of the cordyceps is found to comprise 3'-deoxyadenosine (Cordycepin, CAS No.: 73-03-0), etc.

3'-Deoxyadenosine is a novel broad-spectrum antibiotic. At present, some studies have been conducted on 3'-deoxyadenosine in the field of pharmacology such as antibiotic, anti-inflammation and anti-HIV-1 activities, selective inhibition of *Clostridium*, and immune regulation. Previous studies on the anti-tumor effect of 3'-deoxyadenosine focused on the study of anti-leukemia. In 1997, 3'-deoxyadenosine was used in the United States in a phase-1 clinical trial for treating pre-B and pre-T acute lymphocytic leukemias, whereas subsequent work was not carried out. Currently, there are also some reports about experimental studies of treatment of solid tumors with 3'-deoxyadenosine, but most of them are experiments performed in murine cell lines. Moreover, 3'-deoxyadenosine has relatively low anti-tumor activity when used alone, and has so far not been used as a therapeutic drug for treatment of tumors. Studies in the art have identified that 3'-deoxyadenosine has the effect of regulating the methylation of DNAs in human tumors.

SUMMARY OF THE INVENTION

The technical problem to be solved by the present disclosure is to overcome the defects of the existing technical solutions for treating tumors and provide a new effective choice for the treatment of tumors.

The technical solution of the present disclosure to solve the technical problem is to provide use of a tumor gene methylation regulator in the preparation of anti-tumor drugs.

Wherein, the tumor gene methylation regulator is at least one of laccaic acid, 3'-deoxyadenosine, 5-azacytidine, genistein, and [1-(β-D-ribofuranosyl)-1,2-dihydropyrimidin-2-one] (zebularine).

The 5-azacytidine has a molecular formula of $C_8H_{12}N_4O_5$, a molecular weight of 244.21, and a structure shown by the following formula:

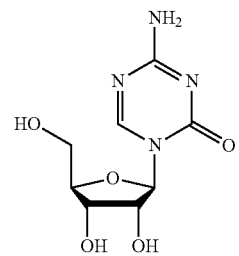

Wherein, the tumor described above is a hematological tumor or a solid tumor.

Wherein, the hematopoietic tumor described above is at least one of leukemia, multiple myeloma, glioma or malignant lymphoma.

Wherein, the solid tumor described above is at least one of breast cancer, lung cancer, gastric cancer, pancreatic cancer, esophageal cancer, colorectal cancer, liver cancer, prostate cancer, uterine cancer, kidney cancer, bladder cancer, or skin cancer.

Wherein, the anti-tumor drug in the use described above contains at least one of anti-tumor active ingredients other than the tumor gene methylation regulator.

Wherein, the anti-tumor active ingredients in the use described above are at least one of 5-fluorouracil, capecitabine, gimeracil, potassium oxonate (Oteracil Potassium), oteracil, tegafur, paclitaxel, docetaxel, epirubicin, doxorubicin, aclarubicin, mitoxantrone, irinotecan, cisplatin, carboplatin, oxaliplatin, nedaplatin, and their respective pharmaceutically acceptable salts.

Wherein, the anti-tumor active ingredients in the use described above are at least one of monoclonal antibody-based anti-tumor drugs such as bevacizumab, aflibercept, pertuzumab, trastuzumab, cetuximab, rituximab, alemtuzumab, and panitumumab.

Further, the anti-tumor active ingredients and the tumor gene methylation regulator in the use described above may be individually packaged.

Also, the present disclosure provides an anti-tumor drug. The anti-tumor drug is prepared using a tumor gene methylation regulator as one of main active ingredients.

Wherein, the tumor gene methylation regulator in the anti-tumor drug described above is at least one of laccaic acid, 3'-deoxyadenosine for suppressing the methylation of tumor suppressor genes, genistein, and [1-(β-D-ribofuranosyl)-1,2-dihydropyrimidin-2-one] (zebularine).

Wherein, the tumor in the anti-tumor drug described above is a hematological tumor or a solid tumor.

Wherein, the hematopoietic tumor in the anti-tumor drug described above is at least one of leukemia, multiple myeloma, glioma or malignant lymphoma.

Wherein, the solid tumor in the anti-tumor drug described above is at least one of breast cancer, lung cancer, gastric cancer, pancreatic cancer, esophageal cancer, colorectal cancer, liver cancer, prostate cancer, skin cancer, uterine cancer, kidney cancer, and bladder cancer.

Further, the anti-tumor drug contains at least one of other anti-tumor active ingredients other than the tumor gene methylation regulator.

Wherein, the anti-tumor active ingredients in the technical solution described above are at least one of platinum anti-cancer drugs, anthracycline anticancer drugs, antimetabolite anticancer drugs, alkaloid anticancer drugs or targeted antibody-based anticancer drugs.

Wherein, the anthracycline anticancer drug described above is at least one of daunorubicin, doxorubicin, epirubicin, mitoxantrone, or their respective various pharmaceutically acceptable salts.

Wherein, the antimetabolite anticancer agent described above is at least one of pemetrexed, tegafur/gimeracil/oteracil, capecitabine, gemcitabine, 5-fluorouracil, or their respective various pharmaceutically acceptable salts.

Wherein, the platinum anticancer drug described above is at least one of cisplatin, carboplatin, oxaliplatin, nedaplatin or their respective various pharmaceutically acceptable salts.

Wherein, the alkaloid anticancer drug described above is a taxane anticancer drug. Further, the taxane anticancer agent is at least one of paclitaxel, docetaxel, cephalomannine, 10-desacetyl paclitaxel, baccatin III or their respective various pharmaceutically acceptable salts.

The anti-tumor active ingredients in the anti-tumor drug are at least one of 5-fluorouracil, capecitabine, gimeracil, potassium oxonate (Oteracil Potassium), oteracil, tegafur, paclitaxel, docetaxel, epirubicin, doxorubicin, aclarubicin, mitoxantrone, irinotecan, cisplatin, carboplatin, oxaliplatin, nedaplatin, or their respective pharmaceutically acceptable salts.

Wherein, the anti-tumor active ingredients in the anti-tumor drug described above are at least one of monoclonal antibody-based anti-tumor drugs such as bevacizumab, aflibercept, pertuzumab, trastuzumab, cetuximab, rituximab, alemtuzumab, and panitumumab.

Apparently, in the case of different tumor types and use of different other anti-tumor active ingredients described above, the relative proportions of various tumor gene methylation regulators and the anti-tumor active ingredients, and their respective specific dosages and application methods can be adjusted depending on specific situations and purposes.

Wherein, the anti-tumor drug described above is an agent prepared by adding a pharmaceutical adjuvant or auxiliary ingredient to the tumor gene methylation regulator as one of main active ingredients.

Wherein, the dosage form of the anti-tumor drug described above is an oral formulation, an injection formulation, a spray formulation or an intravenous drip formulation.

Wherein, the adjuvant or auxiliary ingredient in the anti-tumor drug described above includes one or a combination of several of a diluent, an excipient, a filler, a binder, a wetting agent, a disintegrant, an absorption promoter, a surfactant, a protective agent, an adsorption carrier or a lubricant.

Wherein, the anti-tumor active ingredients and the tumor gene methylation regulator in the anti-tumor drug described above may be compound preparations.

Wherein, the anti-tumor active ingredients and the tumor gene methylation regulator in the anti-tumor drug described above may be individually packaged formulations to be used in combination.

Wherein, the dosage form of the anti-tumor drug described above is an oral formulation or an injection.

Wherein, the injection in the anti-tumor drug described above is an injection solution or a powder injection.

Also, the present disclosure provides a method of treating at least one condition or symptom associated with tumor growth in a human. The method comprises administering a pharmaceutical composition comprising a tumor gene methylation regulator to the human, and administering an effective amount of at least one of other anti-tumor active ingredients in combination.

Wherein, in the method described above, the tumor gene methylation regulator and the anti-tumor active ingredients can be administered to a patient together or administered to the patient separately, and can be deemed as being used in combination, as long as any one of them is administered when the other one of them has a plasma concentration higher than a normal physiological concentration in the patient.

Wherein, the dosage of the tumor gene methylation regulator administered in the method described above is a dosage capable of effectively treating conditions or symptoms associated with tumor growth in combination with the at least one of the anti-tumor active ingredients.

Wherein, in the method described above, the tumor gene methylation regulator is at least one of laccaic acid, genistein, 3'-deoxyadenosine, 5-azacytidine, or [1-(β-D-ribofuranosyl)-1,2-dihydropyrimidin-2-one].

Wherein, in the method described above, the anti-tumor active ingredients are at least one of 5-fluorouracil, gimeracil, tegafur, capecitabine, potassium oxonate, oteracil, paclitaxel, docetaxel, epirubicin, doxorubicin, aclarubicin, mitoxantrone, irinotecan, cisplatin, carboplatin, oxaliplatin, nedaplatin, and various salts thereof.

Wherein, in the method described above, the anti-tumor active ingredients are at least one of bevacizumab, aflibercept, pertuzumab, trastuzumab, cetuximab, rituximab, alemtuzumab, or panitumumab.

Wherein, in the method described above, the tumor is a hematological tumor or a solid tumor.

Wherein, in the method described above, the tumor gene methylation regulator and the anti-tumor active ingredients are administered to the patient by the same or different routes of administration when administered simultaneously.

Wherein, in the method described above, the tumor gene methylation regulator and the other anti-tumor active ingredient are contained in the same formulation or in different formulations when administered to the patient simultaneously by the same route of administration.

Moreover, the present disclosure also provides a method of improving a therapeutic efficacy of a drug for preventing and treating a tumor or reducing an effective dose of the drug for preventing and treating a tumor. A tumor gene methylation regulator is used in combination with an effective amount of at least one of other anti-tumor active ingredients to achieve the purpose of improving the sensitivity of the tumor to the other anti-tumor active ingredient so as to improve the therapeutic efficacy or reducing the effective dose.

Wherein, in the method described above, the tumor gene methylation regulator and the anti-tumor active ingredients can be administered to a patient together or administered to the patient separately, and can be deemed as being used in combination, as long as any one of them is administered when the other one of them has a plasma concentration higher than a normal physiological concentration in the patient.

Wherein, in the method described above, the dosage of the tumor gene methylation regulator administered is a dosage able to improve the therapeutic efficacy of the anti-tumor active ingredients or to reduce the effective dose of the anti-tumor active ingredients.

Wherein, in the method described above, the tumor gene methylation regulator is at least one of laccaic acid, genistein, 3'-deoxyadenosine, 5-azacytidine, or [1-(β-D-ribofuranosyl)-1,2-dihydropyrimidin-2-one].

Wherein, in the method described above, the anti-tumor active ingredients are at least one of 5-fluorouracil, gimeracil, tegafur, capecitabine, potassium oxonate, oteracil, paclitaxel, docetaxel, epirubicin, doxorubicin, aclarubicin, mitoxantrone, irinotecan, cisplatin, carboplatin, oxaliplatin, nedaplatin, and various salts thereof.

Wherein, in the method described above, the anti-tumor active ingredients are at least one of bevacizumab, aflibercept, pertuzumab, trastuzumab, cetuximab, rituximab, alemtuzumab, and panitumumab.

Wherein, in the method described above, the tumor is a hematologic tumor or a solid tumor.

Wherein, in the method described above, the tumor gene methylation regulator and the anti-tumor active ingredients are administered to the patient by the same or different routes of administration when administered simultaneously.

Wherein, in the method described above, the tumor gene methylation regulator and the anti-tumor active ingredients are contained in the same formulation or in different formulations when they are to be administered to the patient simultaneously by the same route of administration.

Finally, the present disclosure also provides a method of preparing the anti-tumor drug described previously.

It is innovatively discovered in the present disclosure that a combination of the tumor gene methylation regulator as a sensitizer with a tumor therapeutic drug can be used for preparing an anti-tumor drug. With the anti-tumor drug of the present disclosure, not only is the therapeutic efficacy enhanced, but the dosage of the tumor therapeutic drug can be significantly reduced simultaneously, thereby remarkably reducing the side effects of the tumor therapeutic drug on the body. The present disclosure can reduce the patients' pain and improve their quality of life, and can also remarkably reduce therapy costs, and therefore has a good prospect of application.

BRIEF DESCRIPTION OF THE DRAWINGS

Extract A in each drawing refers to 3'-deoxyadenosine.

DESCRIPTION OF THE PREFERRED EMBODIMENTS

Figure 1:
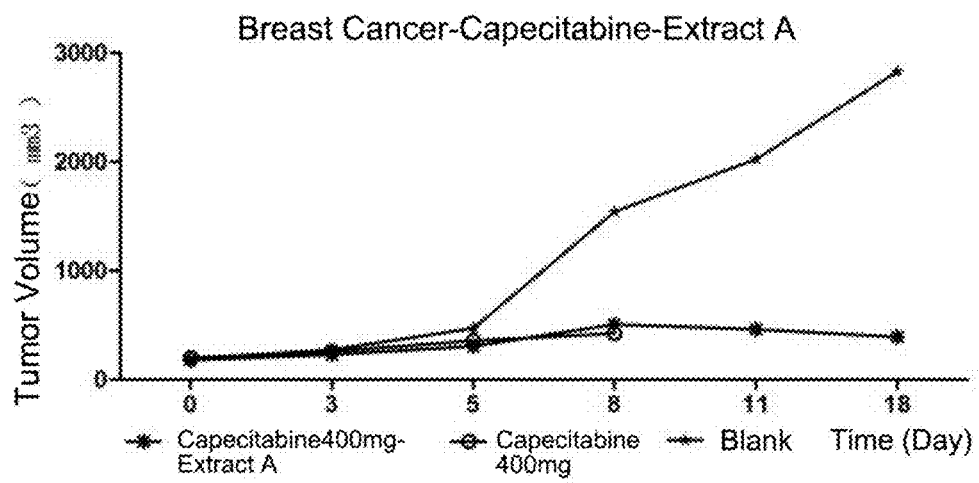
FIG. 1: Results of trials of suppression of breast cancer (MCF-7) with capecitabine and 3'-deoxyadenosine.

In the study of natural 3'-deoxyadenosine, the inventors noticed the similarity of its structure with S-adenosyl methionine (SAM, a methyl donor), and thereby inferred that 3'-deoxyadenosine might be also used as a non-methyl donor to be involved in the process of competing with SAM to bind to DNMTs, change the normal ratio of SAM/SAH (S-adenosyl-L-homocyteine) in cells, and reverse the methylation state of the promoter regions of the tumor suppressor genes, and thereby might inhibit the growth of tumor cells.

On the basis of above, in the previous work, the inventors of the present application treated the in vitro cultured human solid tumor cells (including hepatoma cell line Huh-7, and breast cancer cell lines T47D and MCF-7) with 3'-deoxyadenosine alone and designed a series of trials to confirm that the use of 3'-deoxyadenosine alone could inhibit the proliferation of the abovementioned multiple cell lines, and the mechanism of inhibiting the methylation of tumor suppressor genes to restore the expression of the tumor suppressor genes as proposed by the inventors of the present application was verified at the DNA level. However, its effect was still not satisfactory.

In the subsequent studies, it is innovatively discovered in the present disclosure that tumor gene methylation regulators represented by 3'-deoxyadenosine, such as laccaic acid, 3'-deoxyadenosine, 5-azacytidine, genistein, zebularine or so forth, have the effect of enhancing the sensitivity of tumor cells to the existing tumor therapeutic drugs. In the present disclosure, such tumor gene methylation regulators are referred to as sensitizers for tumor therapeutic drugs. The use of the sensitizers in combination with the tumor therapeutic drugs in the present disclosure can obtain synergistic effects in various tumor models, and can significantly reduce the amount of anti-tumor drugs to be used, thereby reducing the toxic and side effects of the anti-tumor drugs. Based on the above innovative discovery, new anti-tumor drugs can be prepared from the tumor gene methylation regulators and other anti-tumor drugs. A new tumor treatment method is also developed in the present disclosure, that is, the tumor gene methylation regulator is used in combination with other anti-tumor drugs to increase the therapeutic efficacy, or to reduce the amount of other anti-tumor drugs to reduce the toxic and side effects.

The present disclosure will be described in detail below through the introduction of specific embodiments.

Example 1. Results of Experiments of Suppression of Tumor Cells

1. Drugs to be Tested

Compound combinations to be tested: 3'-deoxyadenosine-paclitaxel used in combination, 3'-deoxyadenosine-doxorubicin used in combination, and 3'-deoxyadenosine-cisplatin used in combination.

Control compound groups: 3'-deoxyadenosine, paclitaxel, doxorubicin, and cisplatin.

2. Experimental Design

TABLE 1

Compounds Detected in Different Cells and Concentrations Thereof

| Cell Line | Compound | Concentration (μM) | | | | | |
|---|---|---|---|---|---|---|---|
| Breast Cancer (MCF-7) | 3'-deoxyadenosine | 75 | 50 | 25 | 12.5 | 6.25 | 3.125 |
| | paclitaxel | 125 | 25 | 5 | 1 | 0.2 | 0.04 |
| | doxorubicin | 125 | 25 | 5 | 1 | 0.2 | 0.04 |
| | docetaxel | 10 | 2 | 0.4 | 0.08 | 0.016 | 0.0032 |
| | 3'-deoxyadenosine-paclitaxel | 15.48 | 7.74 | 3.88 | 1.94 | 0.968 | 0.484 |
| | 3'-deoxyadenosine-doxorubicin | 49.2 | 24.6 | 12.3 | 6.16 | 3.08 | 1.54 |
| Liver Cancer (Huh-7) | 3'-deoxyadenosine | 75 | 50 | 25 | 12.5 | 6.25 | 3.125 |
| | cisplatin | 125 | 25 | 5 | 1 | 0.2 | 0.04 |
| | doxorubicin | 125 | 25 | 5 | 1 | 0.2 | 0.04 |
| | nexavar | 10 | 2 | 0.4 | 0.08 | 0.016 | 0.0032 |
| | 3'-deoxyadenosine-cisplatin | 20 | 10 | 5 | 2.5 | 1.25 | 0.0625 |

3. Materials 3.1. Cell Line

Human breast cancer MCF-7, human liver cancer Huh-7;

Features of growth of tumor cells: both MCF-7 and Huh-7 grow adherently to the wall.

3.2. Culture Medium

RPMI 1640 (Invitrogen-22400089); DMEM (Invitrogen-11960077)

FBS fetal bovine serum (Invitrogen-10099141);

Double antibiotics (penicillin and streptomycin) (Invitrogen-15140122)

3.3. Multi-Well Plate

Greiner CELLSTAR® 96-well plate, a flat-bottomed black plate (with a cover and a transparent bottom), #655090.

3.4. Reagents and Instruments for Cell Viability Experiments (1). Promega CellTiter-Glo Luminescent Cell Viability Assay Kit (Promega-G7571).

(2). 2104 EnVision® Plate Reader, PerkinElmer.

4. Experimental Methods and Steps 4.1. Cell Culture

The above tumor cell line derived from ATCC was cultured in an incubator with 5% $CO_2$ at 37° C. The cell line was subcultured twice per week by trypsinization. Cells in the logarithmic growth phase were used for plating.

4.2. Plating (1). The cells were stained with trypan blue, and viable cells were counted.

(2). The concentration of the cells was adjusted to $2 \times 10^4$ cells/ml (about $2.0 \times 10^3$ cells/well).

(3) 100 μl of a cell suspension was added to each well in the culture plate, and a cell-free culture solution was added to the blank control wells.

(4). The culture plate was cultured overnight in an incubator with 5% $CO_2$ and 100% relative humidity at 37° C.

4.3. Preparation of Compound Working Solution (20×) and Treatment of Cells with the Compounds (1). A compound stock solution was taken out of a freezer at −80° C. and thawed at room temperature.

(2). A compound working solution (20×) was prepared.

(3). Dosing: 5 μl of the compound working solution (20×) was taken and added to the cell culture plate. 5 μl of a mixed solution of DMSO-cell culture solution was added to the solvent control and the blank control.

(4). The 96-well culture plate was put back to the incubator for culture for 48 hours.

4.4. CellTiter-Glo Luminescent Cell Viability Assay

The following steps were performed according to the instructions of the Promega CellTiter-Glo Luminescent Cell Viability Assay Kit (Promega-G7571).

(1). A CellTiter-Glo buffer was thawed and brought to room temperature.

(2). A CellTiter-Glo substrate was brought to room temperature.

(3). 10 ml of the CellTiter-Glo buffer was added to one vial of the CellTiter-Glo substrate to dissolve the substrate so as to prepare a CellTiter-Glo working solution.

(4). The substrate was fully dissolved by slow vortexing and shaking.

(5). The cell culture plate was taken out and allowed to stand for 30 minutes so that it was equilibrated to room temperature.

(6) 80 μl of the CellTiter-Glo working solution was added to each well. The cell plate was covered with aluminum foil to protect it from light.

(7). The culture plate was shaken on an orbital shaker for 2 minutes to induce cell lysis.

(8). The culture plate was allowed to stand at room temperature for 10 minutes to stabilize a luminescent signal.

(9). The luminescent signal was detected on a 2104 EnVision plate reader.

4.5 Data Analysis

The inhibition rate (IR) with a test compound was calculated by the following formula: IR (%)=(RLU$_{solvent\ control}$−RLU$_{compound}$)/(RLU$_{solvent\ control}$−RLU$_{blank\ control}$)*100%. The inhibition rates with the compounds at different concentrations were calculated by Excel, and then XLFit software (Equation 205) was used to plot an inhibition curve and calculate related inhibition data, including the minimum inhibition rate, the maximum inhibition rate, the absolute IC$_{50}$, and the relative IC$_{50}$.

5. Results 5.1. Summary of Data and Results of Anti-Proliferation with the Compounds in Cell Viability Experiments

TABLE 2

Data on Suppression of Cell Viability in Human Breast Cancer Cells Viability Experiments

| Cell Type | Drug to be Tested | IC$_{50}$ (μM) |
|---|---|---|
| MCF-7 (human breast cancer) | 3'-deoxyadenosine | 0.85 |
| | paclitaxel | 0.742 |
| | 3'-deoxyadenosine (50 μM) + paclitaxel | 0.952 |
| | 3'-deoxyadenosine (10 μM) + paclitaxel | 0.004 |
| | 3'-deoxyadenosine (5 μM) + paclitaxel | 0.02 |

TABLE 3

Data in Experiments for Suppression of Viability of Human Breast Cancer Cells

| Cell Type | Drug to be Tested | IC$_{50}$ (μM) |
|---|---|---|
| MCF-7 (human breast cancer) | 3'-deoxyadenosine | 0.85 |
| | doxorubicin | 0.51 |
| | 3'-deoxyadenosine (50 μM)-doxorubicin | 1.222 |
| | 3'-deoxyadenosine (10 μM)-doxorubicin | 0.116 |
| | 3'-deoxyadenosine (5 μM)-doxorubicin | 0.386 |

Table 2 showed that for human breast cancer cells, at the identical IC$_{50}$ (i.e., in the case where the inhibition rates of 50% were reached), the amount of paclitaxel used when 3'-deoxyadenosine at 10 μM or 5 μM was combined with paclitaxel (i.e., when the dosage of the drug used was 5 times or 10 times lower than the dosage of the drug used alone) was 1/189 or 1/37 of the amount of the drug used alone, respectively. In other words, when the same inhibition rate was reached, the total dosage of these two drugs was 0.004 μM or 0.02 μM, which was far less than the sum of ½ of the dosages of the two drugs used alone (0.85/2 μM+0.742/2 μM=0.796 μM).

Table 3 showed that for human breast cancer, at the identical IC$_{50}$ (i.e., in the case where the inhibition rates of 50% were reached), the amount of doxorubicin used when 3'-deoxyadenosine at 10 μM or 5 μM was combined with doxorubicin (i.e., when the dosage of the drug used was 5 times or 10 times lower than the dosage of the drug used alone) was ¼ or 1/1.4 of the amount of the drug used alone, respectively. In other words, when the same inhibition rate was reached, the total dosage of these two drugs was 0.116 μM or 0.386 μM, which was far less than the sum of ½ of the dosages of the two drugs used alone (0.85/2 μM+0.51/2 μM=0.68 μM). It was indicated that 3'-deoxyadenosine was synergistic with doxorubicin at 10 μM or 5 μM.

TABLE 4

Data on Suppression of Cell Viability in Human Hepatoma Cells Viability Experiments

| Cell Line | Compound | IC$_{50}$ (μM) | Note |
|---|---|---|---|
| Huh-7 (human hepatoma) | 3'-deoxyadenosine | 1.346 | |
| | doxorubicin | 1.20 | |
| | 3'-deoxyadenosine-doxorubicin | 0.28 | |
| | cisplatin | 5.0 | IC$_{20}$ |
| | 3'-deoxyadenosine (50 μM)-cisplatin (5 μM) | 0.995 | |

Table 4 showed that for human hepatoma, at the identical IC$_{50}$ (i.e., in the case where the inhibition rates of 50% were reached), the total dosage of 3'-deoxyadenosine and doxorubicin used in combination was 0.28 μM, which was far less than the sum of ½ of the dosages of the two drugs used alone (1.346/2 μM+1.2/2 μM=1.27 μM), which indicated that 3'-deoxyadenosine was synergistic with doxorubicin; and the total dosage of 3'-deoxyadenosine and cisplatin used in combination was 0.995 μM, which was far less than the sum of ½ of the dosages of the two drugs used alone (1.346/2 μM+5/2 μM=3.17 μM), which indicated that 3'-deoxyadenosine was synergistic with cisplatin.

Conclusion: One of the important features of tumor cells is their unlimited growth. Therefore, the study of an antitumor drug is first to observe its effect of suppressing the growth of tumor cells. The study results indicate that for human breast cancer cells, 3'-deoxyadenosine combined with paclitaxel has a synergistic effect when 3'-deoxyadenosine is at 10 μM or 5 μM, especially at 10 μM, the amount of paclitaxel used is only 1/189 of the dosage of the drug used alone; and 3'-deoxyadenosine is synergistic with doxorubicin at 10 μM or 5 μM; and for human hepatoma cells, 3'-deoxyadenosine at 50 μM is synergistic with doxorubicin, and 3'-deoxyadenosine at 50 μM is synergistic with cisplatin.

Example 2. Animal Experiments for Suppression of Tumor Viability

1. Experimental Animals

Species: mouse
Strain: BALB/c nude mouse
Gender and Number: female, 7 mice in each group
Week Age and Weight at the Start of Administration: 6 to 8 weeks old, having a weight of 18 to 22 grams.

2. Conditions for Feeding the Experimental Animals

The experiments were started after the animals were fed in the experimental environment for 7 days after arrival. The animals were housed in IVF (independent ventilation system) cages at an SPF animal house (5 animals per cage). In an information card for each cage of animals, the number, gender, strain, date of receipt, administration regimen, experiment number, group type, and start date of experiment, of the animals in the cage were recorded. All the cages, litter, and drinking water were sterilized before use. The cages, feedstuff and drinking water were changed twice a week.

3. Description of Preparation of Trial Models and Treatment with Drugs

Human leukemia cells HL60, human gastric cancer cell line SGC-7901, human breast cancer cells MCF-7, human colon cancer cells HT-29, human lung cancer cells A-549, and human hepatoma cells Huh-7 were routinely cultured in vitro and digested and centrifuged to prepare cell suspensions at a concentration of about 1×10$^7$ cells/mL, respectively, which were inoculated subcutaneously in the right armpits of the mice at 0.2 mL per mouse.

The inoculated well-grown subcutaneously xenografted tumors were removed and cut into tumor tissue blocks with a size of about 2×2×2 mm for later use. After being anesthetized, the mice were placed in the left lateral decubitus position, the tumor tissue blocks were put into the armpits of the mice, the skin was sutured and disinfected, and then the mice were put back into the cages and fed normally. The mice were grouped after the tumors grew to have a diameter of about 7 to 8 mm. Generally, after being grouped, the mice were administered by gavage with a drug or with a blank solution (solvent: 0.9% (g/mL) sodium chloride injection) for continuous 14 days, once per day, administered at a volume of 20 mL/kg. Special situations will be described separately in corresponding examples. The general symptoms of the animals were observed before and after the administration. The longer diameter (a) and shorter diameter (b) of each of the solid tumors were measured twice per week after the first administration, the tumor volume was calculated according to the formula: volume $(V)=\frac{1}{2} \times a \times b^2$, and the animals were weighed. The drug was discontinued after administration for 14 days. On the $7^{th}$ day after stopping the administration, the animals were weighed and then were sacrificed by cervical dislocation, and the solid tumors were removed and weighed. The data obtained were analyzed by SPSS statistical analysis software.

Formula for Evaluation of the Therapeutic Efficacy:

Tumor-growth inhibition rate=(average tumor weight in solvent control group−average tumor weight in administered control group)/average tumor weight in solvent control group×100%.

4. Specific Drug Application for Each Model and Experimental Results

Unless specially stated, the number of nude mice in each group in the following various experiments was seven.

Experiment 1. Experiment of Suppression of Breast Cancer (MCF-7) with Capecitabine and 3'-Deoxyadenosine and Results Thereof Refer to FIG. 1 for experimental results. In the experimental group, the drug (capecitabine 400 mg/Kg+3'-deoxyadenosine 20 mg/Kg (3'-deoxyadenosine was shown as extract A in the figure, similarly in the following figures)) was orally administered to mice with human breast cancer xenografts, and the experimental group showed a tumor inhibition rate of 85% on the $11^{th}$ day of administration compared with the negative control group (normal saline group); the positive control group (capecitabine 400 mg/Kg/day) showed a similar tumor inhibition rate of 86.1%; and in the positive group, 5 experimental animals died on the $11^{th}$ day of the experiment. It was indicated that the combination of capecitabine with 3'-deoxyadenosine had a good tumor-inhibiting effect, and the fact that no experimental animals died on the 11th day also indicated that the toxicity of the combined drugs was significantly reduced.

Figure 2:
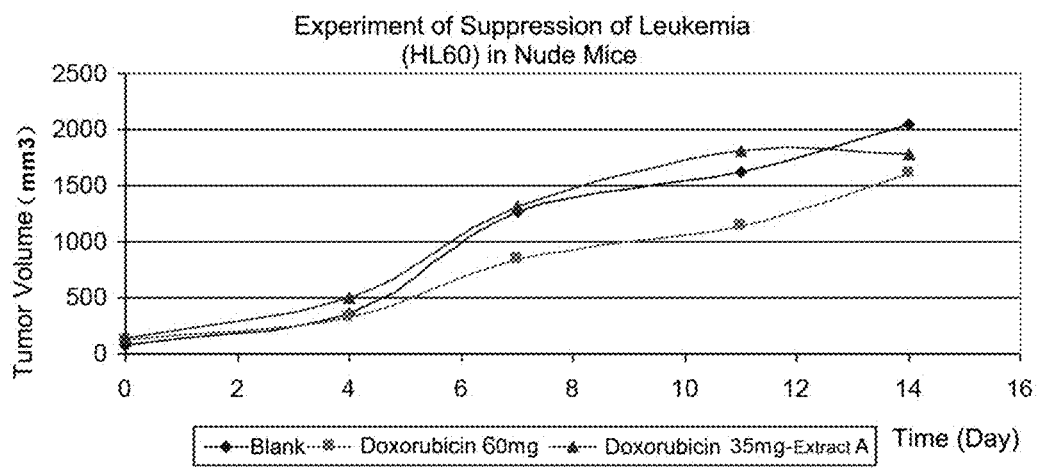
FIG. 2: Results of experiments of suppression of leukemia (HL60) with doxorubicin and 3'-deoxyadenosine.

Experiment 2. Experiment of Suppression of Leukemia (HL60) with Doxorubicin and 3'-Deoxyadenosine and Results Thereof Refer to FIG. 2 for experimental results. The results indicated that the experimental group, in which the drug was orally administered to mice with human leukemia xenografts (doxorubicin 25 mg/week+3-deoxyadenosine 20 mg/kg/week; administration method: doxorubicin at 5 mg/kg/day+ 3'-deoxyadenosine at 4 mg/kg/day, continuously administered for 5 days), showed a tumor-growth inhibition rate of 16.7% on the $14^{th}$ day as compared with the negative control group (normal saline group); and the positive control group (doxorubicin 60 mg/kg/week; 20 mg/kg each time; 3 times/week) showed a tumor-growth inhibition rate of 21.4%, but one experimental animal in this group died on the $14^{th}$ day of the experiment. The amount of doxorubicin used in the experimental group (35 mg/kg/week) was 58.3% of that in the positive control group (60 mg/kg/week). Although the inhibition rate of inhibiting tumors in animals was slightly decreased (21.4% vs. 16.7%), the safety in the experimental group was increased, and no experimental animal died.

Figure 3:
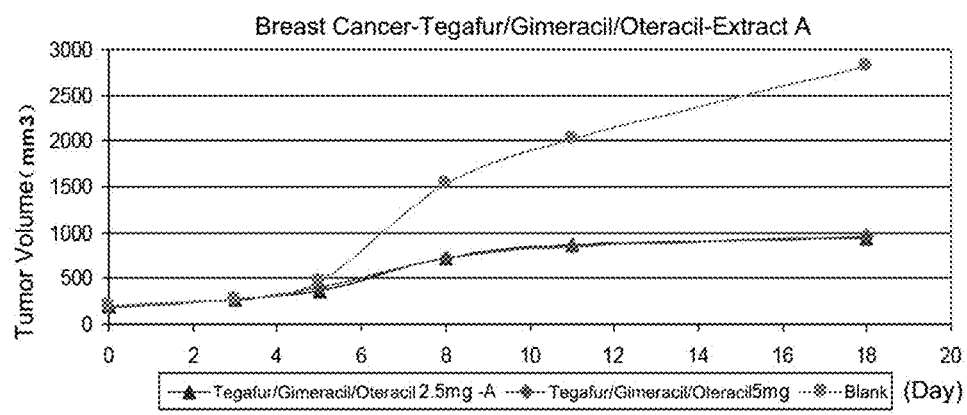
FIG. 3: Results of experiments of suppression of breast cancer (MCF-7) with tegafur/gimeracil/oteracil and 3'-deoxyadenosine.

Experiment 3. Experiment of Suppression of Breast Cancer (MCF-7) with Tegafur/Gimeracil/Oteracil and 3'-Deoxyadenomas and Results Thereof Refer to FIG. 3 for experimental results. In the experimental group, the drug (Tegafur/Gimeracil/Oteracil at 2.5 mg/kg/day+3'-deoxyadenosine at 20 mg/kg/day) was orally administered to mice with human breast cancer xenografts, and the experimental group showed a tumor inhibition rate of 66.9% on the $18^{th}$ day of administration as compared with the negative control group (normal saline group); the tumor inhibition rate in the experimental group was equivalent to the tumor-inhibiting effect (66.2%) of the positive control group (Tegafur/Gimeracil/Oteracil at 5 mg/kg/day); however, one animal in the positive control group died. It was indicated that when Tegafur/Gimeracil/Oteracil was used in a reduced amount but combined with 3'-deoxyadenosine, the tumor-inhibiting effect of a double amount of Tegafur/Gimeracil/Oteracil (5 mg/kg) could be achieved, and moreover the toxicity was reduced.

Figure 4:
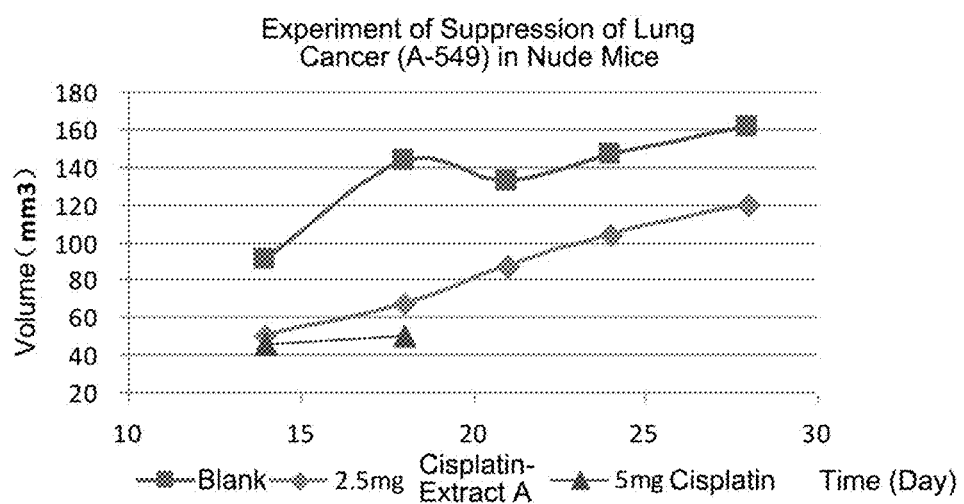
FIG. 4: Results of experiments of suppression of lung cancer (A-549) with cisplatin and 3'-deoxyadenosine.

Experiment 4. Experiment of Suppression of Lung Cancer (A-549) with Cisplatin and 3'-Deoxygenase and Results Thereof On the $14^{th}$ day after inoculation of the mice with lung cancer A-549 cells, xenografted tumor models were successful, and then treated with drugs. Refer to FIG. 4 for experimental results. The results indicated that, in the experimental group, the drug was administered by injection to mice with human lung cancer xenografts (cisplatin at 2.5 mg/kg/day+3'-deoxyadenosine at 20 mg/kg/day), and the experiment continued until the $28^{th}$ day and showed a tumor-growth inhibition rate of 25% as compared with the negative control group (normal saline group); and it was noteworthy that none of the experimental animals in this group died at the end of the experiment.

In contrast, in the positive control group (cisplatin at 5 mg/kg/day), two nude mice died on the $7^{th}$ day; 4 mice died on the $10^{th}$ day; the dosage of cisplatin was reduced to 2.5 mg/kg on the $15^{th}$ day; and a total of 5 mice died on the $18^{th}$ day. Although high-dosage cisplatin (5 mg/kg) had a good inhibitory effect on tumor growth, but more experimental animals died (5/7 animals died) due to its high toxicity, and the experimental work could only be terminated in advance.

Figure 5:
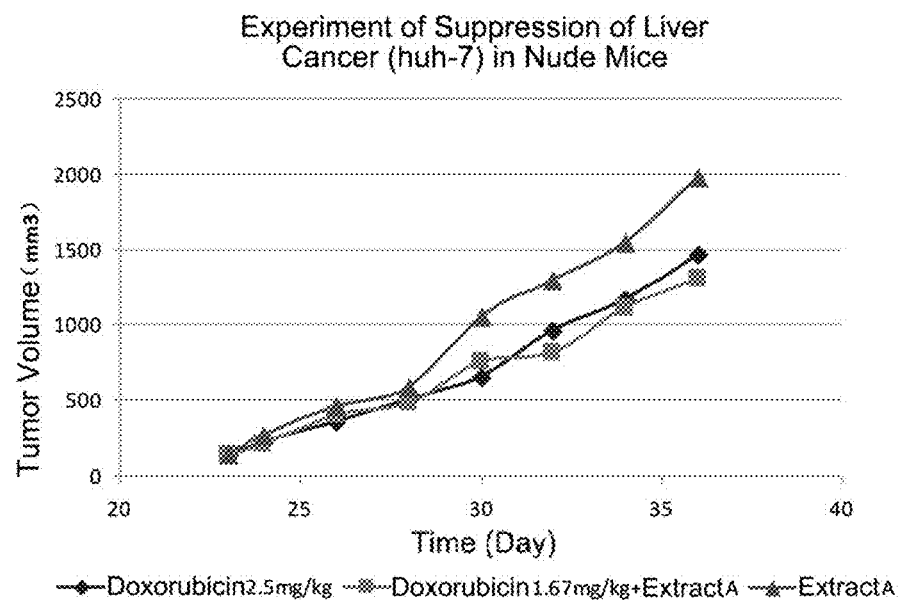
FIG. 5: Results of experiments of suppression of liver cancer (Huh-7) with doxorubicin and 3'-deoxyadenosine.

Experiment 5. Experiment of Suppression of Hepatoma (Huh-7) with Doxorubicin and 3'-Deoxyadenosine and Results Thereof On the $23^{rd}$ day after inoculation of the mice with human hepatoma Huh-7 cells, xenografted tumor models were successful, and then treated with drugs. Refer to FIG. 5 for experimental results. The results indicated that, in the experimental group, the drug was administered intravenously to mice with human hepatoma xenografts (doxorubicin at 1.67 mg/Kg+3'-deoxyadenosine at 12.5 mg/Kg, administered once every two days×6 times); on the 37$^{th}$ day, the experimental group showed a tumor inhibition rate of 33.8% compared with the negative control group (normal saline group); and the tumor-growth inhibition rate in the positive control group (2.5 mg/kg) was 25.7%.

The experimental results showed that although the amount of doxorubicin used in the experimental drug group (1.67 mg/kg) was 66.8% of the amount of doxorubicin used in the positive control group (doxorubicin 2.5 mg/kg), a better tumor inhibition rate was achieved since 3'-deoxyadenosine had a synergistic effect on tumor inhibition with doxorubicin.

Figure 6:
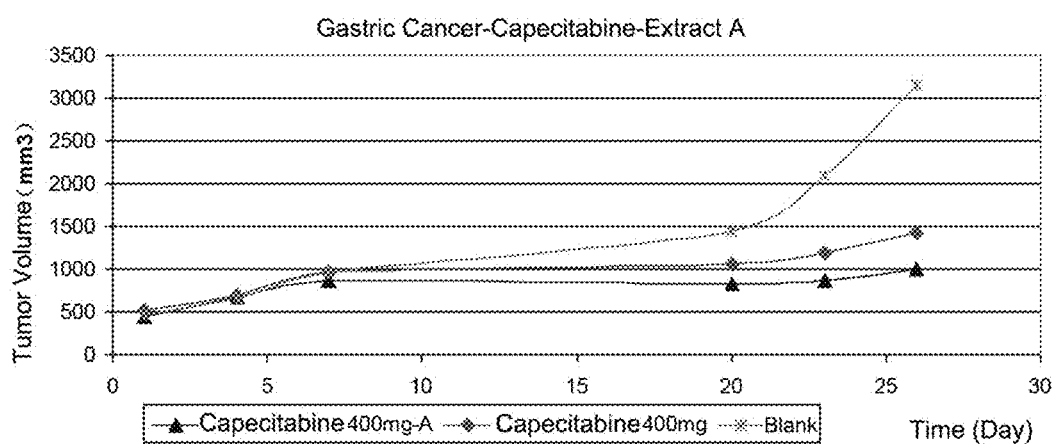
FIG. 6: Results of experiments of suppression of gastric cancer (SGC-7901) with capecitabine and 3'-deoxyadenosine.

Experiment 6. Experiment of Suppression of Gastric Cancer (SGC-7901) with Capecitabine and 3'-Deoxyadenosine and Results Thereof Refer to FIG. 6 for results. The results indicated that, in the experimental group, the drug was orally administered to mice with human gastric cancer xenografts for continuous 14 days (capecitabine at 400 mg/Kg+3'-deoxyadenosine at 20 mg/Kg) after the models were successfully established; on the 27$^{th}$ day, the experimental group showed a tumor inhibition rate of 89.2% compared with the negative control group (normal saline group); and the inhibition rate in the positive control group (capecitabine at 400 mg/Kg) was 57.8%.

The experimental results showed that 3'-deoxyadenosine had a synergistic effect on the inhibition of gastric tumors with capecitabine, so that the tumor inhibition rate was increased by 54%.

Figure 7:
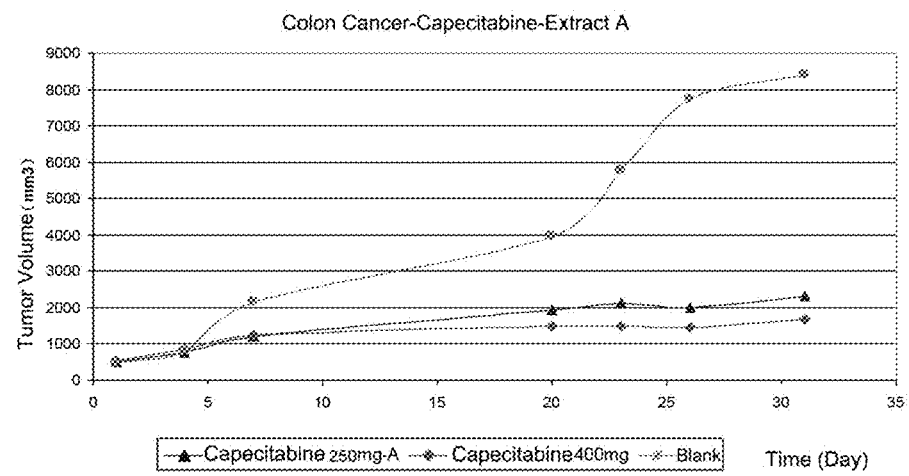
FIG. 7: Results of experiments of suppression of colon cancer (HT-29) with capecitabine and 3'-deoxyadenosine.

Experiment 7. Experiment of Suppression of Colon Cancer (HT-29) with Capecitabine and 3'-Deoxyadenosine and Results Thereof Refer to FIG. 7 for experimental results. The experimental results indicated that, in the experimental group, the drug was orally administered to mice with human colon cancer xenografts for continuous 14 days (capecitabine at 250 mg/Kg+3'-deoxyadenosine at 20 mg/Kg) after the models were successfully established, and on the 31$^{st}$ day, the experimental group showed a tumor inhibition rate of 72.6% compared with the negative control group (normal saline group); and the inhibition rate in the positive control group (capecitabine at 400 mg/Kg) was 80.1%.

The experimental results showed that 3'-deoxyadenosine had a synergistic effect on the inhibition of colon tumors with capecitabine. Although the amount of capecitabine used in the experimental group (250 mg/Kg) was 62.5% of that in the positive control group (capecitabine at 400 mg/Kg), it still showed a good inhibitory effect on colon tumors (72.6% vs. 80.1%) because of the synergistic effect of 3'-deoxyadenosine.

Figure 8:
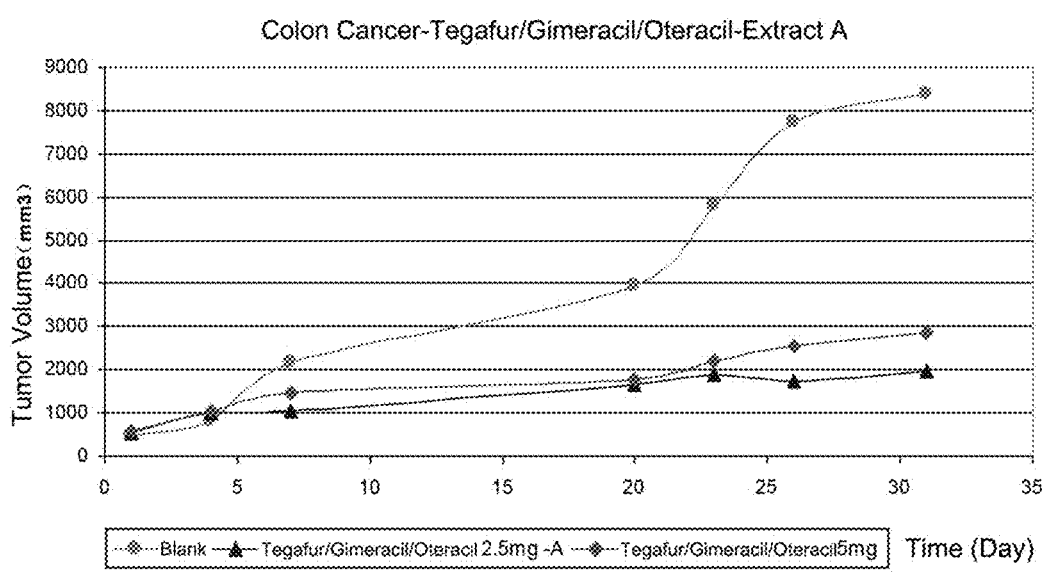
FIG. 8: Results of experiments of suppression of colon cancer (HT-29) with tegafur/gimeracil/oteracil and 3'-deoxyadenosine.

Experiment 8. Experiment of Suppression of Colon Cancer (HT-29) with Tegafur/Gimeracil/Oteracil and 3'-Deoxyadenosine and Results Thereof Refer to FIG. 8 for experimental results. The results indicated that, in the experimental group, the drug was orally administered to mice with human colon cancer xenografts for continuous 14 days (Tegafur/Gimeracil/Oteracil at 2.5 mg/Kg+3'-deoxyadenosine at 20 mg/Kg) after the models were successfully established, and on the 31$^{st}$ day, the experimental group showed a tumor inhibition rate of 76.7% compared with the negative control group (normal saline group); and the inhibition rate in the positive control group (Tegafur/Gimeracil/Oteracil: 5 mg/Kg) was 66.1%. The experimental results showed that 3'-deoxyadenosine had a synergistic effect on the inhibition of colon tumors with Tegafur/Gimeracil/Oteracil. Although the amount of Tegafur/Gimeracil/Oteracil used in the experimental group (2.5 mg/Kg) was less than that in the positive control group (Tegafur/Gimeracil/Oteracil at 5 mg/kg), it still showed a good inhibitory effect on colon tumors (76.7% vs. 66.1%) because of the synergistic effect of 3'-deoxyadenosine.

Figure 9:
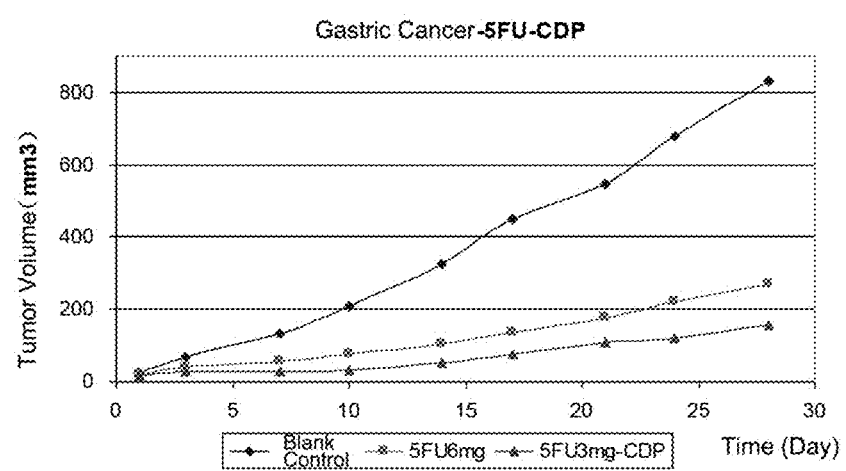
FIG. 9: Results of experiments of suppression of gastric cancer (SGC-7901) with 5-fluorouracil and 3'-deoxyadenosine.

Experiment 9. Results of Experiment of Suppression of Gastric Cancer (SGC 7901) with 5-Fluorouracil and 3'-Deoxyadenosine Each group was administered with a drug once daily (volume 0.2 mL, intravenously) and measured twice per week. In the experimental group (5-fluorouracil at 3 mg/kg+3'-deoxyadenosine at 20 mg/Kg), the drug was administrated intravenously to mice with human gastric cancer (SGC 7901). Experimental results were shown in FIG. 9 (CDP in the figure refers to 3'-deoxyadenosine). On the 28$^{th}$ day of administration, the experimental group showed a tumor inhibition rate of 81.3% compared with the negative control group (normal saline group); and the inhibition rate in the positive control group (5-fluorouracil at 6 mg/kg) was 67.5%.

The experimental results showed that 3'-deoxyadenosine had a synergistic effect on the inhibition of gastric cancer with 5-fluorouracil. Although the amount of 5-fluorouracil used in the experimental group (3 mg/Kg) was reduced by 50% compared with the amount of 5-fluorouracil used in the positive control group (6 mg/kg), it still showed a better inhibitory effect on gastric cancer because of the synergistic effect of 3'-deoxyadenosine.

The invention claimed is:

1. A method of treating at least one condition or symptom associated with tumor growth in human, comprising steps of administering a drug comprising a tumor gene methylation regulator to human, and using an effective amount of at least one of the anti-tumor active ingredients in combination with the tumor gene methylation regulator, wherein the anti-tumor active ingredients comprise capecitabine, the tumor gene methylation regulator comprises 3'-deoxyadenosine, and the tumor is selected from gastric cancer and colon cancer.

2. The method according to claim 1, wherein the tumor gene methylation regulator and the anti-tumor active ingredients can be administered to a patient together or administered to the patient separately, and can be deemed as being used in combination as long as any one of them is administered when the other one of them has a plasma concentration higher than a normal physiological concentration in the patient.

3. The method according to claim 1, wherein a dosage of the tumor gene methylation regulator administered is a dosage capable of effectively treating conditions or symptoms associated with tumor growth in combination with the at least one of the anti-tumor active ingredients.

4. The method according to claim 1, wherein the tumor gene methylation regulator and the anti-tumor active ingredients are administered to a patient by a same or different routes of administration when administered simultaneously.

5. The method according to claim 1, wherein the tumor gene methylation regulator and the anti-tumor active ingredient are contained in a same formulation or in different formulations when administered to a patient simultaneously by a same route of administration.

6. A method for improving a therapeutic efficacy of a drug for treating a tumor or reducing an effective dose of the drug for treating a tumor, wherein a tumor gene methylation regulator is used in combination with an effective amount of at least one of the anti-tumor active ingredients to achieve a purpose of improving sensitivity of the tumor to the anti-tumor active ingredients so as to enhance the therapeutic efficacy or reducing the effective dose and reducing the adverse effect, wherein the anti-tumor active ingredients comprise capecitabine, the tumor gene methylation regulator comprises 3'-deoxyadenosine, and the tumor is selected from gastric cancer and colon cancer.

7. The method according to claim 6, wherein the tumor gene methylation regulator and the anti-tumor active ingredients are administered to a patient together or administered to the patient separately, and can be deemed as being used in combination as long as any one of them is administered when the other one of them has a plasma concentration higher than a normal physiological concentration in the patient.

8. The method according to claim 6, wherein a dosage of the tumor gene methylation regulator administered is a dosage able to improve the therapeutic efficacy of the anti-tumor active ingredients or to reduce the effective dose of the anti-tumor active ingredients.

9. The method according to claim 6, wherein the tumor gene methylation regulator and the anti-tumor active ingredients are administered to a patient by a same or different routes of administration when administered simultaneously.

10. The method according to claim 6, wherein the tumor gene methylation regulator and the anti-tumor active ingredients are contained in a same formulation or in different formulations when administered to a patient simultaneously by the same route of administration.

* * * * *